(12) United States Patent
Dunn et al.

(10) Patent No.: US 8,425,433 B2
(45) Date of Patent: Apr. 23, 2013

(54) DEVICE AND METHOD FOR QUANTIFYING EDEMA

(75) Inventors: Raymond M. Dunn, Shrewsbury, MA (US); Kristen L. Billiar, Worcester, MA (US)

(73) Assignee: University of Massachusetts, Boston, MA (US)

( * ) Notice: Subject to any disclaimer, the term of this patent is extended or adjusted under 35 U.S.C. 154(b) by 644 days.

(21) Appl. No.: 12/148,291

(22) Filed: Apr. 17, 2008

(65) Prior Publication Data

US 2009/0043229 A1    Feb. 12, 2009

Related U.S. Application Data

(63) Continuation-in-part of application No. 11/107,302, filed on Apr. 15, 2005, now Pat. No. 8,147,428.

(60) Provisional application No. 60/562,770, filed on Apr. 16, 2004.

(51) Int. Cl.
*A61B 5/00* (2006.01)

(52) U.S. Cl.
USPC .......................................................... 600/587

(58) Field of Classification Search .................. 600/300, 600/306, 372, 382, 384, 398, 552, 561, 587, 600/595, 553
See application file for complete search history.

(56) References Cited

U.S. PATENT DOCUMENTS

| | | | | |
|---|---|---|---|---|
| 4,159,640 A | | 7/1979 | Leveque et al. | |
| 4,253,449 A | * | 3/1981 | Arkans et al. | 601/152 |
| 4,331,133 A | * | 5/1982 | Arkans | 602/1 |
| 4,418,690 A | * | 12/1983 | Mummert | 601/152 |
| 4,492,234 A | * | 1/1985 | Arkans | 600/490 |
| 4,741,345 A | * | 5/1988 | Matthews et al. | 600/488 |
| 4,771,792 A | * | 9/1988 | Seale | 600/587 |
| 5,170,570 A | * | 12/1992 | Mays, Jr. | 33/512 |
| 5,662,123 A | * | 9/1997 | Goldman | 600/595 |
| 5,788,643 A | * | 8/1998 | Feldman | 600/506 |
| 5,843,007 A | * | 12/1998 | McEwen et al. | 601/152 |
| 6,017,307 A | * | 1/2000 | Raines | 600/300 |
| 6,186,962 B1 | | 2/2001 | Lloyd et al. | |
| 6,283,916 B1 | * | 9/2001 | Leahy et al. | 600/300 |
| 6,294,519 B1 | * | 9/2001 | Oeltgen et al. | 514/16 |
| 6,315,745 B1 | * | 11/2001 | Kloecker | 602/13 |
| 6,409,662 B1 | * | 6/2002 | Lloyd et al. | 600/300 |
| 6,415,525 B1 | * | 7/2002 | Watkins | 33/759 |
| 6,468,237 B1 | * | 10/2002 | Lina | 601/150 |
| 6,544,202 B2 | * | 4/2003 | McEwen et al. | 601/150 |
| 6,551,252 B2 | * | 4/2003 | Sackner et al. | 600/536 |
| 6,577,897 B1 | * | 6/2003 | Shurubura et al. | 600/547 |
| 6,632,192 B2 | * | 10/2003 | Gorsuch et al. | 604/6.04 |
| 6,723,051 B2 | * | 4/2004 | Davidson et al. | 600/454 |
| 6,740,038 B2 | * | 5/2004 | Davidson et al. | 600/438 |
| 2002/0173711 A1 | * | 11/2002 | Walton | 600/398 |
| 2003/0220556 A1 | * | 11/2003 | Porat et al. | 600/407 |

* cited by examiner

*Primary Examiner* — Max Hindenburg
(74) *Attorney, Agent, or Firm* — McCarter & English, LLP

(57) ABSTRACT

The preferred embodiments of the present invention are directed at a device that provides a reliable, accurate and quantifiable measure of a patient's edema. The device improves on the current method of digital manipulation by evaluating the pitting phenomena in a user-independent manner. The output of the device allows a physician to categorize edema into at least ten different levels of severity. The systems of the present invention provides the ability to distinguish between tissues of varying viscosity.

25 Claims, 10 Drawing Sheets

DEVICE AND METHOD FOR QUANTIFYING EDEMA

CROSS REFERENCE TO RELATED APPLICATIONS

The present application is a continuation-in-part application of U.S. Utility application Ser. No. 11/107,302 filed Apr. 15, 2005 and claims the benefit of U.S. Provisional Application No. 60/562,770, filed Apr. 16, 2004. The entire contents of the above applications are incorporated herein by reference.

BACKGROUND OF THE INVENTION

Venous Stasis Disease (VSD), characterized by edema, occurs when there is an obstruction and/or incompetence of the venous valves or veins in the arms and legs. Edema, an atypical accumulation of fluid in the interstitial space, is caused by fluid leaking out of the vasculature into the surrounding tissue subsequent to the buildup of pressure in the venous walls. While uncomfortable for the patient and capable of leading to other serious complications, edema can be an indicator of the extent of VSD.

One of the complications resulting from VSD are leg ulcers. If the valves are damaged the blood can backflow causing high pressure in the veins. Under these conditions fluids that are normally retained in the veins leak out, resulting in swelling in the legs. This swelling can prevent oxygen, which is carried in the blood and necessary for the healing process, from reaching the wound site. Compression therapy is often used as treatment with the rationale that if the excess fluid can be squeezed out, oxygen can return and the wound can heal.

Currently, there is no device which is capable of measuring the severity of edema in a feasible, economical and quantifiable way. The most widely used clinical method for assessing the amount of edema is digital manipulation. This assessment is accomplished by pressing into the patient's leg and qualitatively evaluating the degree of pitting. Pitting is the indentation in the swollen tissue that remains following removal of pressure from the edemous area. Due to the altered tissue composition resulting from edema, there is a putty-like consistency to the tissue, and the tissue remains in the indented position for seconds to minutes before returning to its original form. The doctor performing the test assesses the depth of the indention, how much force is required to reach the tibia, for example, how long the tissue takes to return to the original state, and skin quality. The level of edema is described using a ranking system of one to four (slight to severe). Despite the qualitative nature of this technique, it is still considered the state of the art for edema assessment. There is a continuing need to improve the assessment of edema that is reliable and economical.

SUMMARY OF THE INVENTION

The preferred embodiments of the present invention relate to a device that provides a reliable, accurate and quantifiable measure of a patient's edema. The device improves on the current method of digital manipulation by evaluation of the pitting phenomena in a user-independent manner. The output of the device in accordance with a preferred embodiment of the present invention allows a physician to categorize edema into at least ten different severities, for example, thereby improving on digital manipulation's subjective one to four scale. The systems of the present invention provide for the ability to distinguish between tissues of varying viscosity.

The systems and methods of the present invention include a tonometer which can be used as an office device to assess swelling of the extremities, such as the lower leg. It includes an electromechanical or optical sensor that when applied to the swollen region of the leg provides a measure of the tone (i.e., pressure) in the leg. After a region of tissue is compressed for a selected period of time the applied pressure is released. The rate of return or relaxation of the tissue after release of pressure indicates quantitatively the condition of the tissue. The slower the rate of return, the more severe the edema. Thus, the device can provide a quantitative measure of displacement and applied pressure as well as these parameters as a function of time. The pressure in the leg is a function of the amount of edema, for example, which can be correlated to the amount of oxygen at the wound site. The reading received can be used to determine if compression therapy is a valid treatment and if so, what amount of compression is needed. The patient's healing progress can then be assessed by periodic measurements, for example, weekly to determine if swelling has decreased.

In accordance with an aspect of the present invention, a preferred embodiment of the device is used for assessing compression therapy which is often used to treat leg ulcers. The regions of the leg with the ulcer is wrapped in elastic compression bandages. Several layers of bandages may be necessary to achieve the pressure required to control or inhibit fluid flow in the veins or tissue in and around the ulcer. A preferred embodiment device includes a miniaturized pressure sensor that can measure and monitor the amount of pressure resulting from compressing a region of the leg, for example. This device can be used to accurately gauge the amount of pressure being applied by the bandages for compression therapy.

The tonometer device in accordance with a preferred embodiment of the present invention for assessing edema in the lower extremities is easy to use and can be inexpensively manufactured. It can be sufficiently low power to be run on batteries and can have a wired or wireless connection to a computer or a computer network in a clinic, physician's office or hospital. This device provides an office tool used to determine if compression therapy is a valid treatment for a particular leg ulcer, for example. The device is also an indicator of congestive heart failure as the fluid retained in the peripheral extremities is correlated with the severity of a patient's heart condition.

A further embodiment of the invention provides a device to measure the severity of pitting edema. To obtain a measurement, the user holds the device against the patient's tissue and uses his thumb to depress a tissue indenter, creating an indentation. The device measures and displays the depth of indentation on a display screen as an indicator of edema severity. A microprocessor program outputs the distance measured when the force increases rapidly and the displacement of the tissue indenter ceases to increase. The device also displays the force required to reach maximum displacement, and the return time of the tissue following displacement. Return time is an indicator of whether edema is or is not present in a patient. A clinician can collect the values from this device over time to determine whether a patient's swelling is increasing or decreasing.

The complete device is compact, ergonomic and reduced cost. It consists of a handheld component that makes contact with the patient's tissue, and contains force and distance transducers. A remote display box contains batteries and a microprocessor to provide a portable battery powered system with wireless network.

The excess interstitial fluid buildup from edema changes the properties of the tissue. Edematous tissue is characterized by an increase in resistance to pressure, as well as a severe reduction of elasticity, which gives the tissue a putty-like quality. When pressure is applied to edematous tissue, it may remain depressed for several minutes before returning to its original state. This phenomenon is known as "pitting." One of the primary ways to evaluate peripheral edema is to observe the response of edematous tissue to depression. Medical professionals classify the level of edematous severity using a scale ranging from 1 (least severe) to 4 (most severe).

The present invention provides a device that can objectively monitor the severity of edema in extremities. The primary use of the device is to collect a patient's edema measurements for a comparison over time to determine if any increase or decrease in swelling has occurred. The most important objectives for the device are to improve accuracy and objectivity by reducing user-dependence and minimizing individual bias in measurements. The most important parameters for measuring edematous pitting, such as depth of pitting, relaxation time, and force needed to depress the tissue.

The foregoing and other features and advantages of the system and method for quantifying edema will be apparent from the following more particular description of preferred embodiments of the system and method as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The preferred embodiments of the present invention are directed at a device that provides a reliable, accurate and quantifiable measure of a patient's edema. The device improves on the current method of digital manipulation by evaluating the pitting phenomena in a user-independent manner. The output of the device allows the physician to categorize edema into at least ten different severities, thereby improving on digital manipulation's subjective one to four scale.

Figure 1:
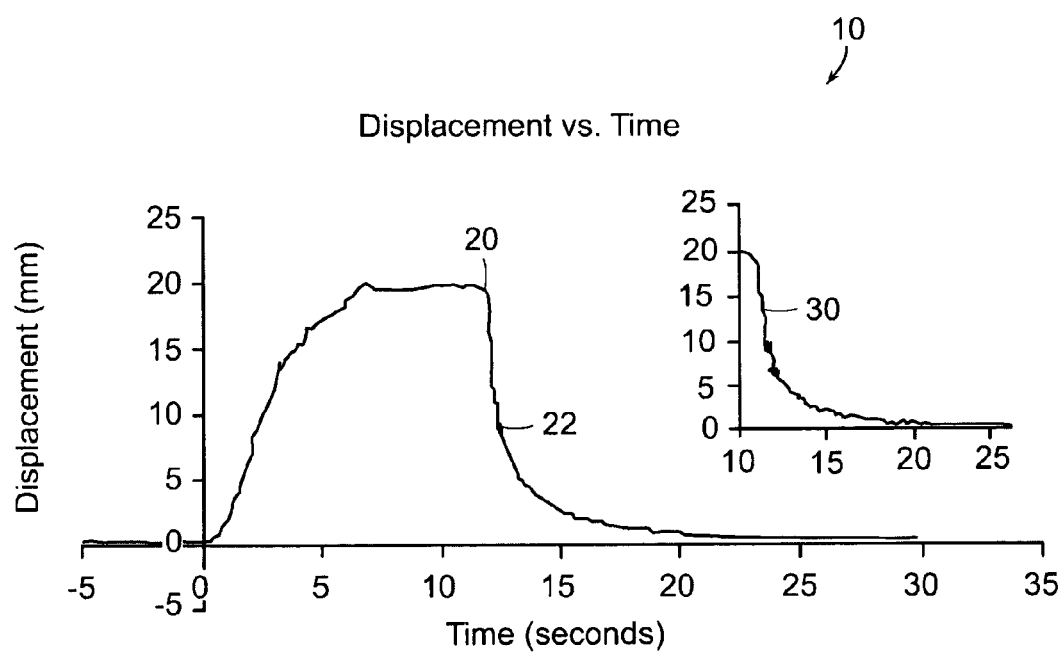
FIG. 1 graphically illustrates displacement into a sample material versus time during measurement of the pitting phenomenon in accordance with a preferred embodiment of the present invention.

During an assessment of pitting, a clinician presses his/her thumb into the tissue, for example, the lower leg. The displacement of the tissue peaks, then as the thumb is released the skin recovers due to the viscoelastic properties of the tissue. These viscoelastic properties, and thus the time-course of the recovery, are dependent upon the severity of edema. FIG. 1 illustrates the displacement if an exemplary material versus time during measurement of the pitting phenomenon. In FIG. 1, indention into the material occurred during the first 7 seconds. The indenting member was then held constant at the maximum depth for 5 seconds. At the twelve second mark, the force was released. The sample material recovered to its original dimensions over the following 20 seconds. The point 22 on the curve represents the "half-time," that is the time that it takes for the material to return to half its original depth which is used as the measure of recovery time in accordance with a preferred embodiment of the present invention. The half time can also be displayed on the relaxation curve only at 30. The relaxation point can be selected by the user to provide a more diagnostically useful indicator depending on the type of condition being evaluated.

In accordance with a device of a preferred embodiment of the present invention, the time it takes for the skin to return half way to its undeformed position is used as the measure of the recovery time and the measure of severity of edema.

Figure 2A:
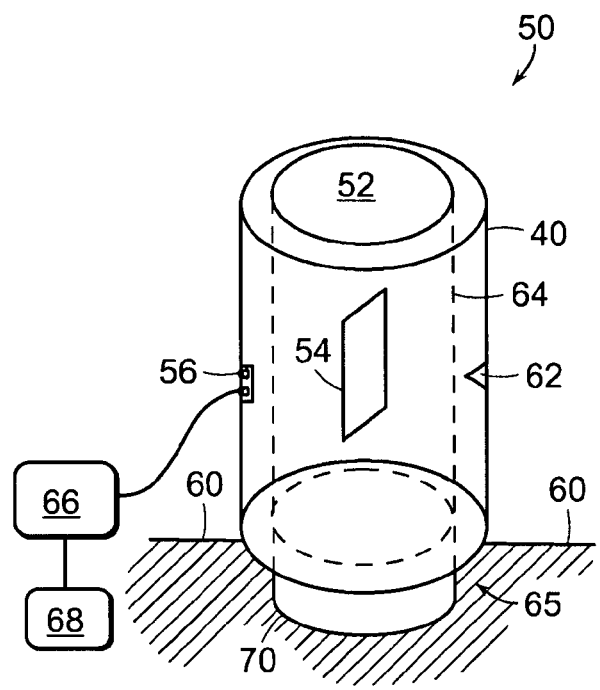
FIGS. 2A and 2B illustrate, schematically, devices used to quantify edema in accordance with a preferred embodiments of the present invention.

FIG. 2A illustrates a schematic of a device 50 in accordance with a preferred embodiment of the present invention. The device 50 in accordance with a preferred embodiment can include two concentric cylinders. The inner cylindrical member 64 acts as the "indenter" or member which moves vertically, and the outer tube 40, the base or housing is stationary. A light emitting diode (LED) or other light source 62 and a matched photoreceptor or detector 56 are attached to the base cylinder. Attached to the inner cylinder is a barrier 54, arranged so as the inner member 64 lowers into the tissue 65 the barrier lowers and gradually blocks the light collected by the detector 56. The barrier 54 can be mounted to an opening in the cylinder 64 that allows light to pass through. The barrier 54 can be made of an opaque material such as plastic that has a linear or non-linear variation in thickness to provide a variable transmissiveness. This arrangement results in a voltage change which is a function of the depth of the member 64. The detector is connected to an amplification and filter circuit 66. The output voltage can be displayed on a display 68, an oscilloscope or collected by a data acquisition board for processing and display at a later time period. Other types of electromechanical sensors such as capacitive sensors, Hall effect sensors, LVDTs, etc. can also be used to measure the response of the tissue to displacement.

In operation, the thumb can depress upper surface 52, for example, presses the member 64 into the tissue 60, causing the barrier 54 to block a portion of the light from the LED 62 to the detector 56. The base 40 is used to stabilize the device and mount the detector, light source 62, cylinder and barrier 54.

To evaluate a device in accordance with a preferred embodiment of the present invention, measurements were taken to assess the ability of the device to distinguish between three materials with varying viscoelastic properties. The materials chosen were three pieces of viscoelastic foam (Latex Mattress Center, San Francisco): one dry, one saturated with vegetable oil, and the last saturated with 5W-40 motor oil. These three materials represent and are indicative of a range of severities of edema. Each sample responded differently in terms of the force required to indent the material and rate of return after being released.

The device was situated to rest upon the foam surface. The operator then pressed the member 64 into the foam using his thumb. The force was applied for a three second interval and then released. An oscilloscope (Tektronix, TDS210) was used to view a time versus voltage output as the member 64 returned and the half time was calculated. The output value of the device was also recorded.

To validate the difference in viscoelastic properties between the materials by an independent measurement system, the recovery from indentation was also measured using a Laser Displacement System (LDS)(LK-081, Keyence Corporation, Woodcliff Lake, N.J.), and the output value recorded.

For the validation measurements using the LDS, the average half time (±SD) for the foam infused with motor oil was 2.88±0.51 seconds, with vegetable oil was 2.21±0.38 seconds, and dry was 1.09±0.43 seconds. This data demonstrates the substantial increase in half-time of the material as the viscosity of the fluid in the foam increases.

Figure 3:
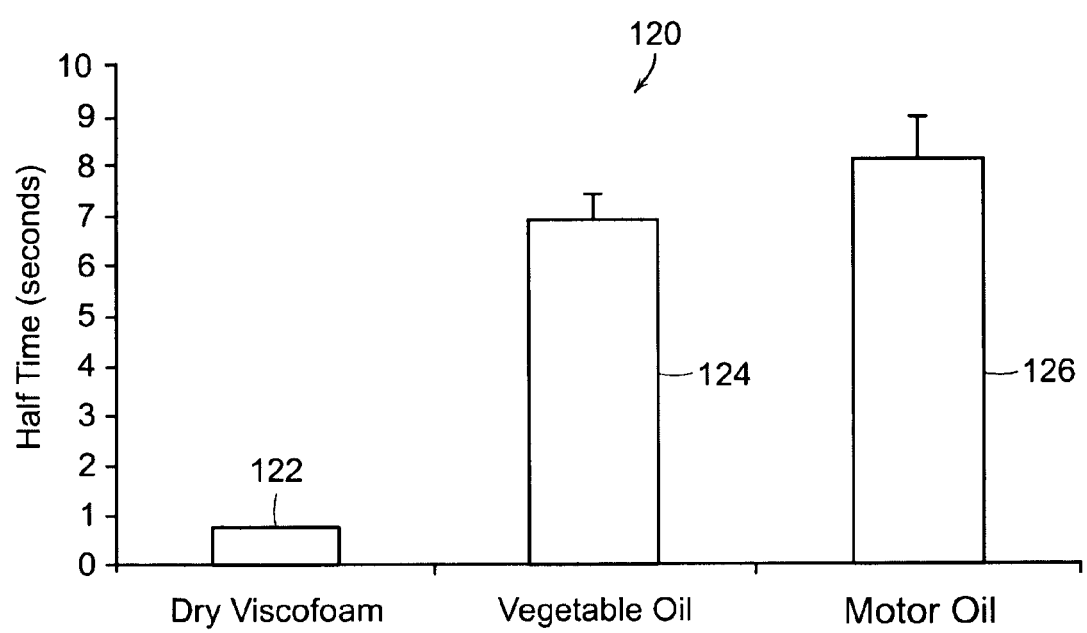
FIG. 3 illustrates data collected using a system to measure edema in accordance with a preferred embodiment of the present invention.

The half-time data recorded using the device in accordance with a preferred embodiment of the present invention is shown in FIG. 3. Half-time to recovery from indentation data is measured using the device. The measurement data shows clear distinctions between the three foam samples, two of which were saturated with liquids of increasing viscosity. These measurements indicate that the device can be used to distinguish between different severities of edema which produce similar changes in viscoelastic response to tissues in patients with venous statis disease.

In the validation measurement, the device demonstrates its ability to clearly differentiate between materials with viscoelastic properties in the range of mild to moderate edema. This result indicates that the methodology described herein may be useful for assessing the severity of edema in patients with VSD. The methods and systems in accordance with a preferred embodiment of the present invention improve upon current methods for assessing edema in that it is inexpensive, portable, easy to use, and provides a quantitative measure.

Figure 2B:
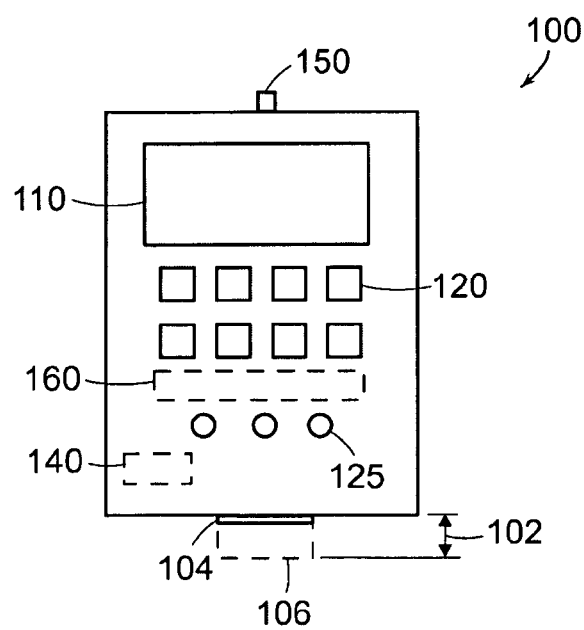

The variability of the half-life values for each material was very small (coefficient of variation <10%). However, the arrangement of the barrier and optical elements in the device in accordance with a preferred embodiment of the present invention produces a non-linear response which limits the useful range of the device. The highest intensity light is directly between the LED and the detector. As the barrier is lowered, the amount of light blocked increases. In another preferred embodiment in accordance with a preferred embodiment of the present invention, the output is linearized and the device further machined to tighter specifications which increases its accuracy and precision. To further determine the validity of this method for assessing edema, the half-time values from clinical studies can be correlated to the severity of edema as assessed by multiple clinicians. A preferred embodiment device can be miniaturized and the amount of applied pressure can be automated as shown in FIG. 2B. The processor and display can be incorporated into the device housing 100 to display numerical values indicative of the severity of edema. The data for a given patient can be acquired and stored electronically. The device 100 can be operated by a battery 140, has a display 110, buttons or other actuators 120 to control parameter selection and operation, small lights (LEDs) 125 to indicate status of measurement, displacement member 104 which can be displaced a distance 102 to a second position 106.

Figure 4:
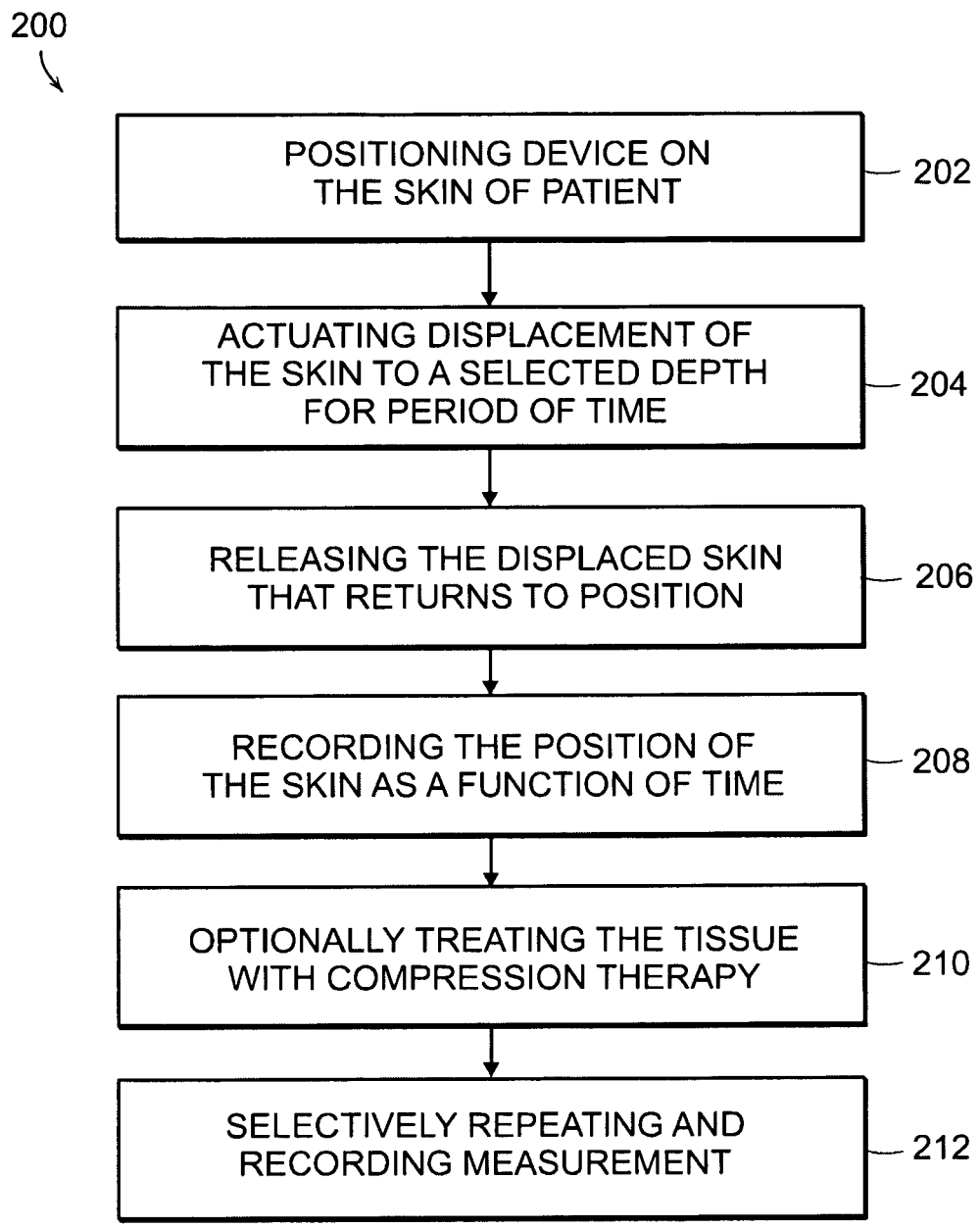
FIG. 4 illustrates a method of using the device to diagnose the condition of edematous tissue.

Illustrated in FIG. 4 is a process sequence illustrating a preferred method 200 of quantitatively measuring edema in accordance with the invention. After positioning the device 202 on the skin of the patient, the user either manually or electronically actuates the device to displace the skin and underlying tissue to a selected depth for a selected period of time 204. The user then releases the pressure exerted by the device which allows the tissue and skin to return 206 to a position. The device records the position of the skin as a function of time 208. The user can optionally treat the patient with compression therapy and/or medication 210. The user can also elect to repeat and record additional measurements 212.

Figure 5:
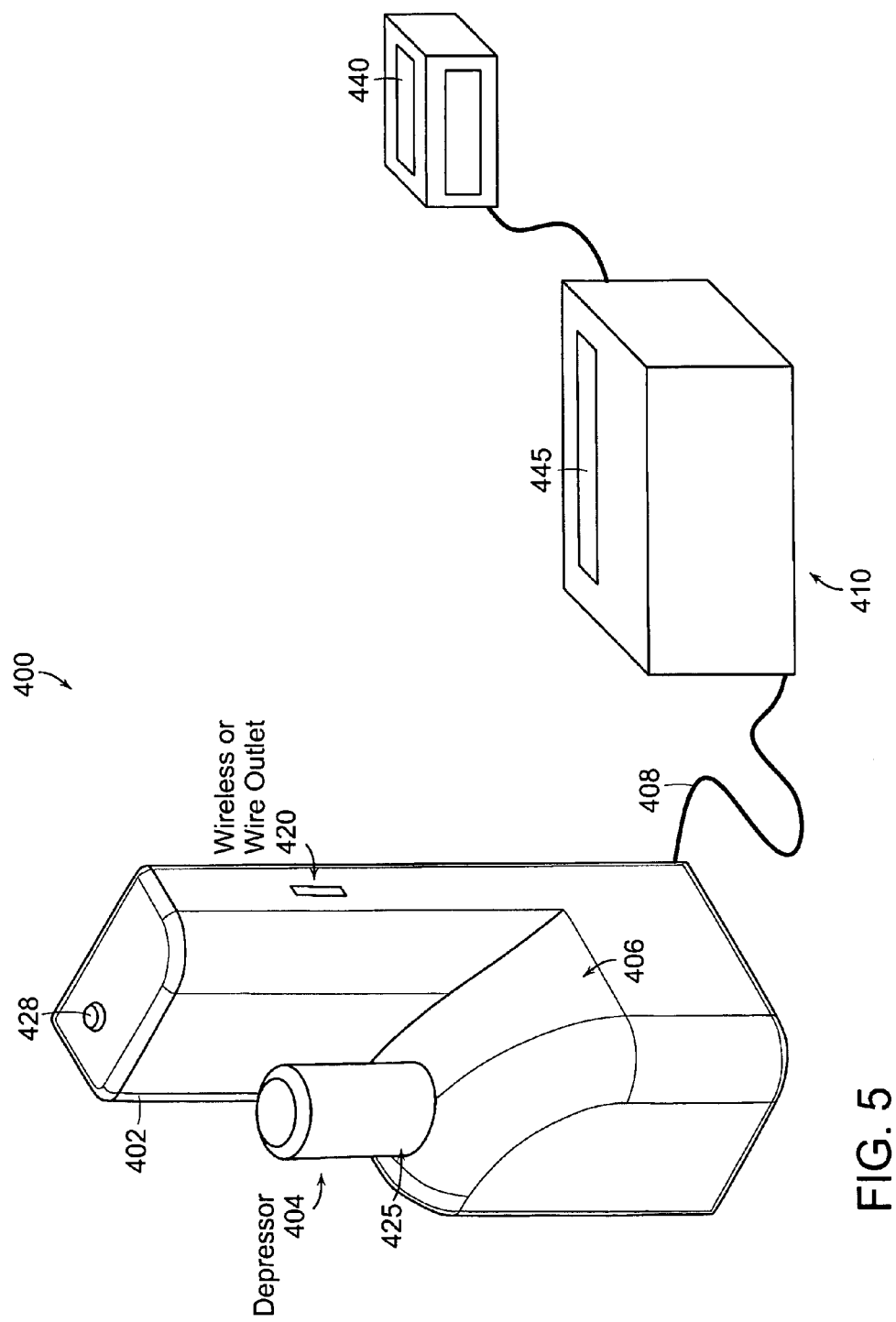
FIG. 5 is a perspective view of a preferred embodiment of the invention.

A preferred embodiment of the invention uses a portable system 400 weighing less than 10 pounds illustrated in FIG. 5. A load cell by Measurement Specialties is for the force measurement.

The displacement transducer can be a linear encoder made by U.S. Digital. The metrics for the distance transducer were cost, size and weight, range and resolution, interface, and contact/non-contact. In this device, a capacitive sensor emits an electric field and detects changes in the field to measure changes in displacement. Thus, the capacitive sensor measures displacement without making direct contact with the surface of interest. Alternatively, a linear encoder contains a plunger, which needs to move up and down to detect changes in displacement. Thus, the linear encoder measures changes in displacement using a contact measurement.

The preferred device has an indenter 404 that makes the depression into the edematous tissue. If the linear displacement transducer makes a non-contact measurement, the device can be mounted on the indenter. If the displacement transducer makes a contact measurement, a connection between the displacement transducer and the indenter ensures that motion of the indenter corresponds to the motion of the displacement transducer.

The edema measurement device 400 measures force against time, distance against time, and force against distance. In addition, it will take a measurement at the peak rate of change of force. Lastly, the device measures the tissue return time to indicate the presence of edematous tissue. A microcontroller 410 processes the data and measures time.

The TI MSP430F449 can be used as the controller 410 as it contains the features that needed; ultra-low power consumption, an ADC, 60 KB of flash memory, 2 KB of data memory, and 48 I/O pins.

The components in the edema measurement device are powered by battery source in housing 410 or from computer 440 connected to controller 410. Alternatively, an AC wall outlet to provide power and portability can be used.

The housing 402 contains the linear encoder, force transducer, thumb depressor 404, indenter, and associated wireless transceiver or cable connector 420. A cable 408 can leave the housing and terminates in the controller housing, which contains the microcontroller, associated circuitry, and batteries.

The housing 402 can be a molded polymer or metal. A polymer or plastic housing is lightweight, has a low coefficient of friction, wear-resistant, and has been approved for use by the FDA for medical devices. The dimensions of the components determined the geometry of the final housing, which was designed to fit the contours of a hand that can fit with slot 406. The base of the device is flat and allows the clinician to make solid contact with the edematous tissue. To use the device, the clinician places his thumb around the front of the device over the thumb depressor. The thumb depressor (0.75 inches in diameter) to be comfortable for an average thumb size based on anthropometric data. The indenter, the piece that makes contact with the tissue, is 0.5 inches in diameter. The total volume of housing 402 is less than 100 cubic inches and preferably less than 50 cubic inches.

The thumb depressor is inserted into a hole 425 on the front of the device and connected to an internal indenter 452. The smaller hole 428 on top of the device is an outlet for the linear encoder probe 426. The slot on the side of the device is an outlet for the wires to the microcontroller or can be a wireless receiver.

The thumb depressor sits on top of the load cell 450, which connects to the tissue indenter 452. Pressing on the thumb depressor into the tissue results in a force measurement that corresponds to the stress the clinician applies to the depressor. The depressor moves smoothly up and down 1¼ in. which represents the full range of motion of the linear encoder.

Figure 6:
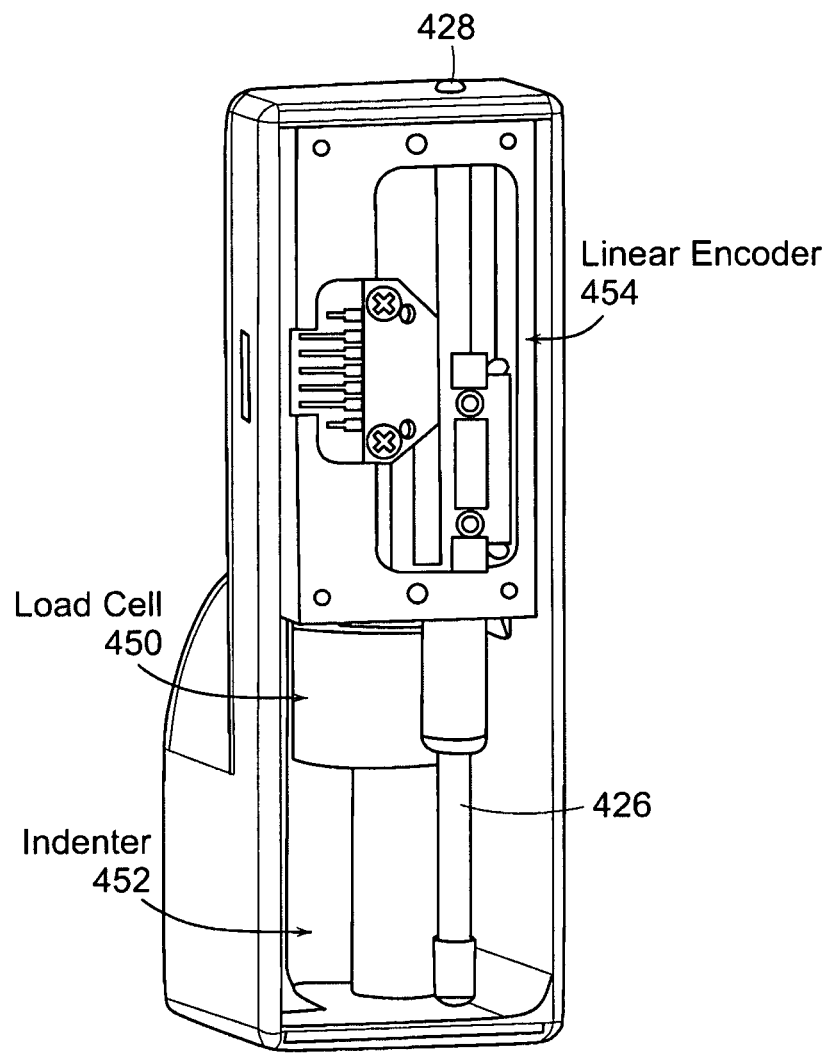
FIG. 6 is a cut away view of the embodiment of FIG. 5.

FIG. 6 shows the relationship between the depressor, indenter, and load cell. The linear encoder fits snugly into the back of the device with the plunger 426 of the encoder close to the bottom of the device. The depressor makes contact with the top of the load cell which is sandwiched between the depressor and the indenter. The indenter connects to the plunger of the linear encoder so that relative motion of the encoder corresponds to relative motion of the indenter, load cell, and depressor unit. The user will notice the plunger of the linear encoder poking out the top of the device at 428 as the plunger moves up and down.

The microcontroller, additional circuitry, and batteries are located in a separate housing connected to the main housing by one wire. The control box contains a display 445 such as an LCD that displays the output values for edema severity and has buttons for the clinician to begin and clear measurements on the microcontroller. The clinician may place the controller to the side during measurement and reference once the measurements are complete.

Figure 7:
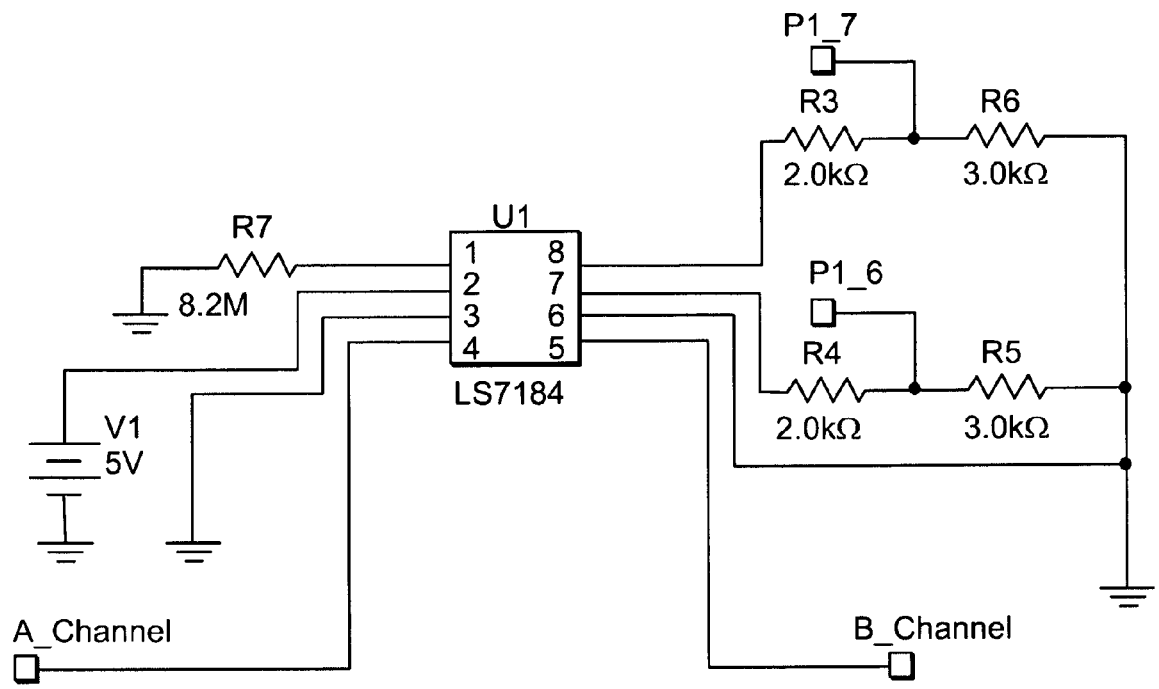
FIG. 7 is a schematic circuit diagram for a distance measurement.
Figure 8:
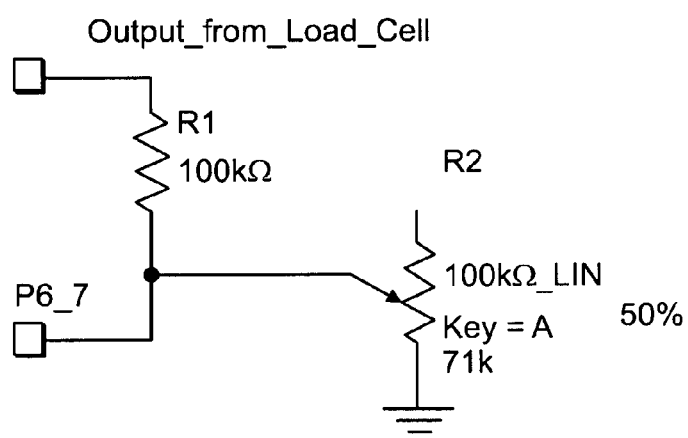
FIG. 8 is a schematic circuit diagram for a load cell.

Circuit designs for the distance measurement and the load cell are shown in FIGS. 7 and 8, respectively. The circuitry for both the distance measurement and the force measurement was to scale the maximum voltage down from 5V to 2V from the load cell and 3V from the linear encoder. Scale down of the voltage from the load cell to 2V was used because the maximum voltage that the analog-to-digital converter (ADC) would convert was 2.5V. Since any voltage greater than 2.5V would be interpreted as 2.5V, we chose to use a 0.5V margin to prevent the voltage from exceeding approximately 2V. The maximum voltage that can be input to the microcontroller was 3.3V, so scale down of the voltage from the linear encoder to 3V provided us with a 0.3V margin. Eight AA batteries power the linear encoder, LS 7184, and load cell. Since this voltage is greater than 5V and the maximum recommended voltage to power the load cell is 5V, the group used a voltage regulator, the 7805A, to protect the components from voltages that are higher than 5V.

The cable that connects the linear encoder to the circuit board contains four wires connected to four of the five pins on the linear encoder. Pin 1 on the linear encoder is connected to ground on the circuit board. Pin 3 carries Channel A from the linear encoder to Pin 4 on the LS 7184. Pin 4 on the linear encoder carries the +5V DC signal from the output of the voltage regulator to the linear encoder. The last pin, Pin 5, carries Channel B and is connected to Pin 5 on the LS 7184.

One of the output signals from the LS 7184 indicates the distance that the plunger is traveling. This output comes from Pin 8 of the chip, and it is a series of $5V_{peak}$ digital square pulses, each of which represents $\frac{1}{250}^{th}$ of an inch.

The other output signal from the LS 7184 indicates the direction in which the plunger is moving. This output comes from Pin 7 of the chip, and is either a 0V DC signal or a 5V DC signal, depending on whether the plunger is moving out or in (down or up), respectively.

Since the maximum voltage that can be an input to a microcontroller is 3.3V, we used two identical voltage dividers, shown in, to scale the voltages down to a range of 0-3V. Each of these voltage dividers consisted of a 2 kΩ resistor, which was connected to the output of the chip, and a 3 kΩ resistor, connected to ground. The inputs to the microcontroller came from the nodes between the 2 kΩ and 3 kΩ resistors. The output from the voltage divider from Pin 7 on the LS 7184 connects to P1.6 on the microcontroller, or Pin 11. Pin 8 connects to P1.7 on the microcontroller, or Pin 9 on EXT. It was desirable to place an 8.2MΩ resistor between Pin 1 and ground because the 8.2MΩ resistor adjusts the width of the square pulses to 120 µs.

Preferably, the load cell outputs an analog signal that ranges between 1V and 4V, where 1V would correspond to 0 lbs and 4V would correspond to 10 lbs. Since 4V is too large to input to the microcontroller, we again used a voltage divider, which consisted of a 100 kΩ resistor and a 100 kΩ potentiometer that was set to 71 kΩ, to scale the voltage down to a maximum of 2V. FIG. 8 shows the schematic for the force sensor circuit. The output from the voltage divider goes to P6.7 on the microcontroller, or Pin 1.

The program for the microcontroller determines the distance the probe moved, determine the force applied to the sensor, determine the rate of change of the applied force, calculate the velocity at which the probe was moving, and measure tau. The outputs of the microcontroller were the maximum depth of indentation in two-hundred-fiftieths of an inch, the maximum force on a scale between 0 and 4095, and tau in hundredths of seconds. The frequency of the clock is 8 MHz.

Figure 9:
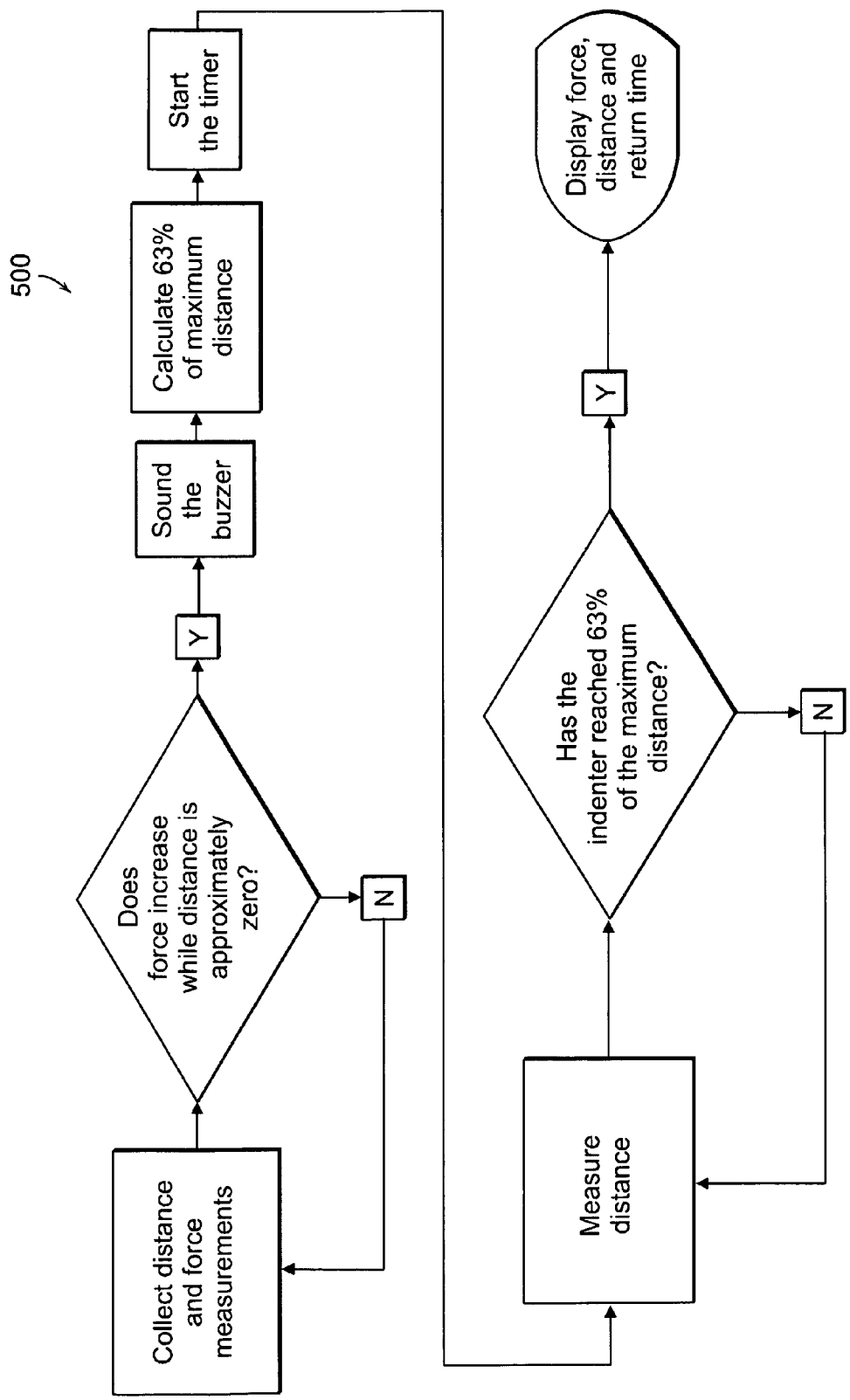
FIG. 9 is a process sequence for a measurement in accordance with the invention.

FIG. 9 shows the flowchart for the software program 500. The measurement of the distance traveled is not included in the program because it occurs whenever the microcontroller detects a rising edge of the input signal, and the calculation of velocity force, and the rate of change of the force with time occurs every 10 ms throughout the program. Until the clinician presses the start button (on housing 410), they can move the probe, but the distance the probe moves will not be saved. Once the clinician presses the start button, as the probe is pushed, the distance is measured is displayed on the LCD in two-hundred-fiftieths of an inch.

Figure 10A:
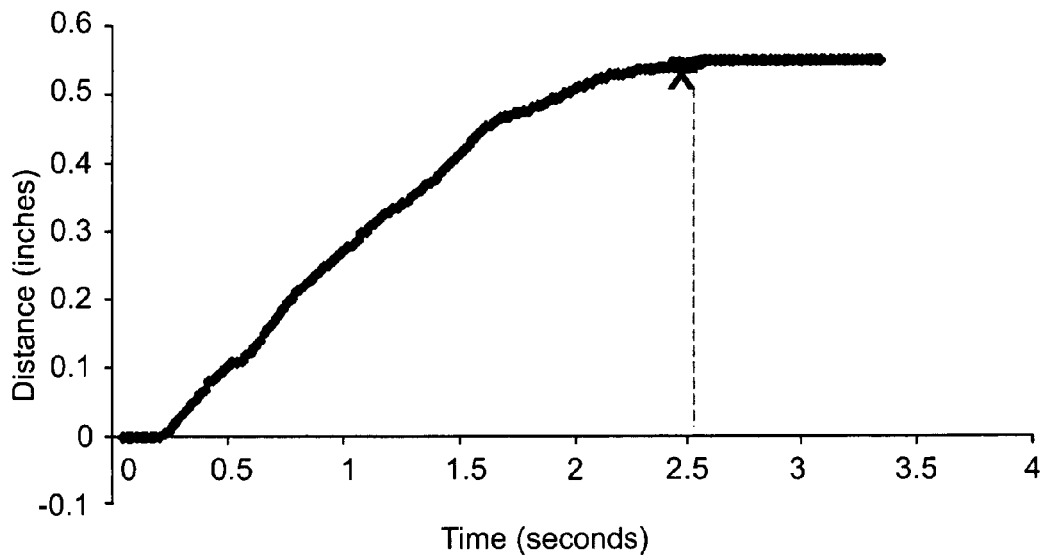
FIGS. 10A, 10B and 10C are graphical illustrations of distance and force measurements in accordance with the invention.
Figure 10B:
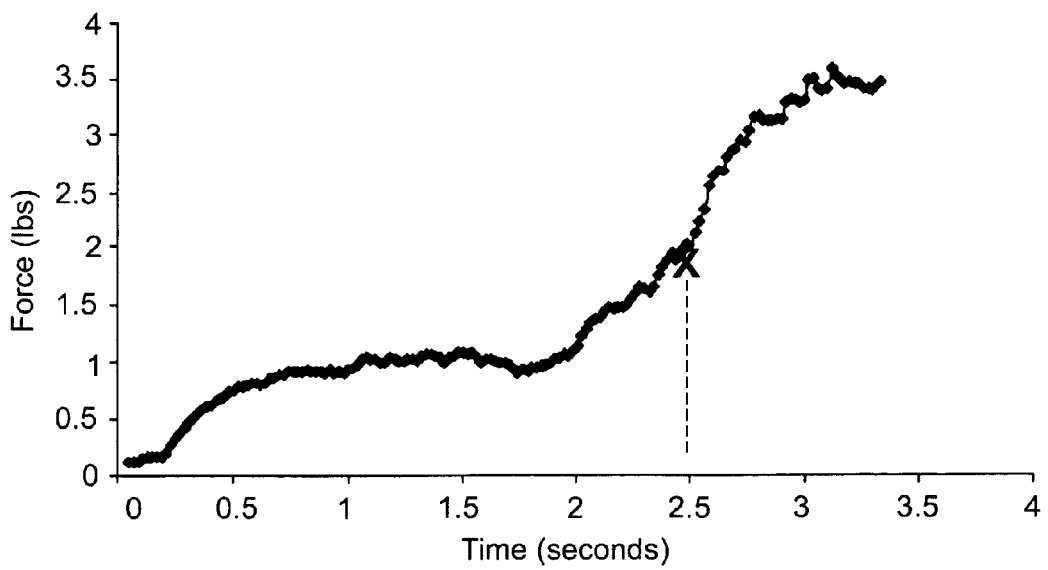

FIG. 10A shows the maximum distance depressed for a sample, which is compared to the force measurement shown in FIG. 10B. The force on the tissue also increases, particularly as the user begins to reach the point of maximum compression. At this point, the force increases at a greater rate than previously. The force increases exponentially until the user realeases the thumb depressor. At the indicated point, the graph shows how the force vs. time increases exponentially because the user has reached the bottom of the point where the indentation can be depressed. By monitoring force vs. time, the user has not stopped pressing before reaching the maximum compression point.

Figure 10C:
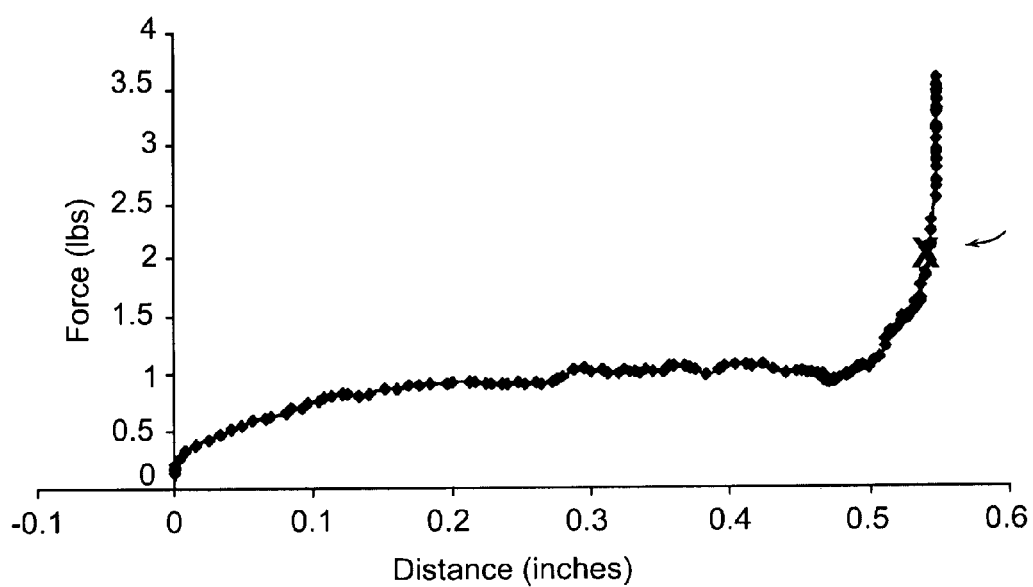

Combining the two primary values of the measurements of force vs. distance can be used to show an easily defined point where once can identify that distance has reached a maximum, and force is increasing exponentially. FIG. 10C shows how the graphs remain relatively constant until the point where distance and force reach their peak. The X in FIG. 10C corresponds to 2.5 seconds where distance and force were marked in FIGS. 10A and 10B. By programming the algorithm in the microcontroller to monitor force and distance over time simultaneously, one can identify the point has depressed though all of the edematous tissue and collect a maximum distance. This value will correspond to the severity of edema in each patient.

The claims should not be read as limited to the described order or elements unless stated to that effect. Therefore, all embodiments that come within the scope and spirit of the following claims and equivalents thereto are claimed as the invention.

What is claimed is:

1. An edema measurement device comprising:
   a handheld housing including a battery that provides power to the device;
   a displacement member attached to the housing that is actuated to displace edematous tissue of a patient to a displaced position relative to the housing; and
   a sensor in the housing that measures displacement of the displacement member as a function of time such that the sensor measures displacement of the edematous tissue during relaxation from the displaced position, the sensor generating tissue relaxation displacement data indicative of a level of edema in the tissue.

2. The device of claim 1 wherein the sensor comprises an optical sensor.

3. The device of claim 1 further comprising an electromechanical actuator.

4. The device of claim 3 wherein the actuator comprises an LVDT (linear variable differential transformer).

5. The device of claim 1 further comprising a display and a processing circuit in the handheld housing.

6. The device of claim 1 further comprising a device actuator on the handheld housing that controls device operation.

7. The device of claim 1 further comprising a programmable processor in the handheld housing, the processor being programmed to record displacement data after the removal of a force imparted to the tissue by the displacement member.

8. The device of claim 1 further comprising an electronic storage device.

9. The device of claim 1 wherein the displacement member is configured to contact skin tissue on an arm or leg of the patient.

10. The device of claim 1 further comprising a wireless connection.

11. The device of claim 1 wherein the device is connected to a computer.

12. The device of claim 1 wherein the housing includes a displacement measurement circuit connected to the sensor.

13. The device of claim 1 wherein the housing includes a force sensor that is connected to a force measurement circuit.

14. The device of claim 1 wherein the housing has a volume less than 100 cubic inches.

15. The device of claim 1 wherein the housing further comprises a depressor to manually displace the member.

16. The device of claim 1 further comprising an electronic controller connected to the housing.

17. The device of claim 1 further comprising a processor that computes force as a function of distance.

18. An edema measurement device comprising:
   a handheld housing including a displacement circuit and a battery that provides power to the device;
   a displacement member attached to the housing that is actuated to displace edematous tissue of a patient to a displaced position relative to the housing;
   depressor mounted to the housing that manually displaces the displacement member; and
   a sensor in the housing that is connected to the displacement circuit that measures displacement of the displacement member as a function of time such that the sensor measures displacement of the edematous tissue during relaxation from the displaced position, the displacement circuit generating tissue relaxation displacement data indicative of a level of edema in the tissue.

19. The device of claim 18 further comprising a controller attached to the handheld housing.

20. The device of claim 18 further comprising a force sensor that measures a force exerted by the displacement member on the tissue.

21. The device of claim 20 wherein the force sensor is connected to the depressor and measures a force exerted by the displacement member on the tissue.

22. The device of claim 18 further comprising a memory in the handheld housing for data storage.

23. The device of claim 22 wherein the memory records force and displacement data before and after application of force to the tissue with the displacement member.

24. The device of claim 20 wherein the force sensor comprises a load cell.

25. The device of claim 18 wherein the displacement member is configured to contact skin tissue or an arm or leg of the patient.

* * * * *